United States Patent
Mane et al.

(10) Patent No.: US 7,723,284 B2
(45) Date of Patent: May 25, 2010

(54) SOLID PERFUMED PREPARATION IN THE FORM OF MICROBEADS AND THE USE THEREOF

(75) Inventors: Jean Mane, Grasse (FR); Loîc Bleuez, Saint Laurent du Var (FR); Guy Delpech, Grasse (FR); Nathalie Hoc, Grasse (FR); Jean-Michel Hannetel, Grasse (FR); Pascal Dailland, Grasse (FR)

(73) Assignee: V. Mane Fils, Bar sur Loup (FR)

( * ) Notice: Subject to any disclaimer, the term of this patent is extended or adjusted under 35 U.S.C. 154(b) by 1350 days.

(21) Appl. No.: 10/239,022

(22) PCT Filed: Mar. 16, 2001

(86) PCT No.: PCT/FR01/00798

§ 371 (c)(1),
(2), (4) Date: Nov. 6, 2002

(87) PCT Pub. No.: WO01/70283

PCT Pub. Date: Sep. 27, 2001

(65) Prior Publication Data

US 2004/0106536 A1    Jun. 3, 2004

(30) Foreign Application Priority Data

Mar. 20, 2000  (FR)  .................... 00 03535

(51) Int. Cl.
*A61K 8/28* (2006.01)
*A61K 8/00* (2006.01)
*G01N 35/08* (2006.01)
*A61L 9/04* (2006.01)
*A61K 8/18* (2006.01)

(52) U.S. Cl. ............... 512/1; 512/2; 512/4; 512/25; 436/55; 424/66

(58) Field of Classification Search ........... 512/4, 512/1, 2, 25; 436/55; 424/66
See application file for complete search history.

(56) References Cited

U.S. PATENT DOCUMENTS

| 2,102,849 | A | * | 12/1937 | Kokatnur ................. 264/13 |
| 3,985,298 | A | | 10/1976 | Nichols |
| 4,610,927 | A | | 9/1986 | Igarashi et al. |
| 4,885,175 | A | * | 12/1989 | Zibell ..................... 426/5 |
| 4,906,488 | A | | 3/1990 | Pera |
| 4,954,285 | A | * | 9/1990 | Wierenga et al. .......... 510/101 |
| 4,973,422 | A | * | 11/1990 | Schmidt .................. 510/337 |
| 5,066,419 | A | * | 11/1991 | Walley et al. ............. 510/396 |
| 5,188,838 | A | | 2/1993 | Deleuil et al. |
| 5,225,188 | A | * | 7/1993 | Abrutyn et al. ............ 424/66 |
| 5,380,527 | A | * | 1/1995 | Legrow et al. ............. 424/401 |
| 5,455,035 | A | * | 10/1995 | Guerrero et al. ........... 424/401 |
| 5,567,416 | A | * | 10/1996 | Sato et al. ................ 424/76.4 |
| 5,662,935 | A | * | 9/1997 | Motta ..................... 424/465 |
| 5,807,584 | A | * | 9/1998 | Thiesse et al. ............. 424/489 |
| 5,871,765 | A | * | 2/1999 | Johnson et al. ............ 424/409 |
| 6,024,943 | A | * | 2/2000 | Ness et al. ................ 424/59 |
| 6,335,021 | B1 | * | 1/2002 | Cavazza .................. 424/401 |
| 6,492,025 | B1 | * | 12/2002 | Chopra et al. ............ 428/402.21 |
| 6,927,201 | B2 | * | 8/2005 | Hsu et al. ................ 510/441 |

FOREIGN PATENT DOCUMENTS

EP    0 317 658    5/1989

* cited by examiner

*Primary Examiner*—Lore Jarrett
(74) *Attorney, Agent, or Firm*—Stites & Harbison PLLC; Stephen J. Weyer; William E. Jackson

(57) ABSTRACT

The invention concerns a solid perfumed preparation with high persistency in the form of microbeads and comprising a volatile aromatic raw material, or a mixture of volatile aromatic raw materials, and one or several fusible excipients. Said preparation can further comprise one of the following constituents: one or more polymers dispersible in the melted mass formed by the constituents of the preparation, one or more mineral additives, one or more surfactants, one or more antioxidants, one or more colouring agents. The invention can be used in cosmetics and in household product industries.

16 Claims, No Drawings ial in a controlled manner and over a long period (persistence), and can be used even in an aggressive medium, and thus with many common cosmetic carriers or in household products such as detergents.

SOLID PERFUMED PREPARATION IN THE FORM OF MICROBEADS AND THE USE THEREOF

FIELD OF THE INVENTION

The present invention relates to solid fragranced preparations in the form of microbeads. These preparations allow the release of a volatile, or even highly volatile, aromatic raw material in a controlled manner and over a long period (persistence), and can be used even in an aggressive medium, and thus with many common cosmetic carriers or in household products such as detergents.

BACKGROUND OF THE INVENTION

Fragranced preparations, i.e. preparations comprising volatile aromatic raw materials, have been used for a long time and in many products, in particular in cosmetic products and household maintenance products.

However, it is sought to further maintain or improve the odoriferous action of these preparations, in particular the persistence of the odor. Specifically, in standard formulations, the aromatic raw materials have a very short persistence on the skin or the hair, in particular on account of their volatility, which is sometimes very high. However, it is important, particularly in cosmetics, but also in household products, to have available preparations whose pleasant odor lasts a long time.

Moreover, many carriers used in cosmetic compositions or household products are aggressive media, which may degrade or alter the aromatic raw materials, which are fragile compounds. This is the case in particular for compositions based on thioglycolate, α-hydroxy acids, hydrogen peroxides, amine compounds, aqueous ammonia, dihydroxyacetone, sunscreens, aluminum salts or strong bases. It is thus just as important to have available volatile aromatic raw materials in a form such that they conserve their odoriferous properties, in particular the persistence of the odor, even in such aggressive media. This allows them to be used in combination with a larger number of common cosmetic carriers or common household products, and thus in a larger number of applications in the cosmetics industry and in the household products industry.

To satisfy this ever-increasing concern for conservation of the odor in the preparation or final composition and for increasing the persistence of this odor, the Applicant has thus sought to develop a preparation incorporating a vehicle for carrying volatile aromatic molecules or raw materials which is capable of protecting them from the external medium and of promoting the conservation and persistence of the odor.

SUMMARY OF THE INVENTION

The Applicant has found that these objectives can be achieved by combining the volatile aromatic raw material(s) with one or more meltable cosmetic excipients, and by a presentation in the form of stable solid microbeads of high persistence.

Depending on the choice of compounds, the preparation according to the invention allows a release of volatile aromatic raw materials that is two to twenty times longer than that of the same aromatic raw materials in traditional packaging, for example in the form of an immediate-release alcoholic solution. Thus, the preparation according to the invention has high persistence, i.e. it allows a significant improvement in the persistence of a fragrance, for example in a hydrogel or in another cosmetic or household carrier.

Another advantage of the preparation according to the invention is that it allows the use of volatile aromatic raw materials that are considered to be unstable in a highly aggressive medium and that are therefore not currently used at all or not in an efficient manner. Specifically, when they are packaged traditionally, they lose their odoriferous properties and thus their advantage. The possibility of using them in such media has the consequence of increasing the creativity, in olfactory terms, regarding the fragrancing of difficult cosmetic carriers or household products: a much wider choice of aromatic raw materials and of cosmetic carriers or household products that may be used will be made available.

Presentations of chemical products in the form of microbeads are already known. However, these are usually mineral products, such as fertilizers, which are relatively insensitive to heat or humidity, and thus relatively nonfragile, and which are made in this form of microbeads simply for greater ease of use.

Presentations of pharmaceutical active principles in the form of microbeads are also known. However, the problems raised in this field are specific and different than the problems raised by the use of volatile raw materials. Specifically, in the pharmaceutical field, it is a matter of modifying the release kinetics of an active principle, without modifying its physicochemical properties and thus its pharmacological activity. The problem of the volatility of the raw material is therefore not addressed.

Thus, the presentations of products in the form of solid microbeads of the prior art are themselves designed for a simple ease of use, or to modify the release kinetics of an active principle forming part of a pharmaceutical composition. The problems associated with the volatility of the raw materials, and with their sensitivity to the medium, are neither raised nor, even less so, solved.

In the case of fragranced preparations, the preparation in the form of solid microbeads makes it possible simultaneously to shape volatile compounds, to protect these compounds against oxidation phenomena and other impairments, to obtain high persistence, and to allow the use of the preparation with common cosmetic carriers or household products even if they are aggressive. Furthermore, microbeads also have the advantage of having an appealing visual impact, of having a uniform distribution as regards the diameter and shape, and of being able to combine different particle size populations.

MORE DETAILED DESCRIPTION

The invention thus concerns a solid fragranced preparation with improved persistence in the form of microbeads, comprising a volatile aromatic raw material or a mixture of volatile aromatic raw materials, and one or more meltable excipients. The invention also concerns the process for manufacturing such a preparation, the use of such a preparation in cosmetics or in household products, and a cosmetic formulation or household product comprising such a preparation.

In the present patent application, the expression "volatile aromatic raw material" will denote, without distinction, a volatile aromatic raw material or a mixture of volatile aromatic raw materials.

A meltable excipient is an excipient that changes to the liquid state under the effect of heat. The meltable excipients that may be used are meltable excipients of cosmetic grade or adapted for use in household products, i.e., as nonlimiting examples, detergents (washing powder and washing liquid), softening products and products for treating textiles.

The volatile aromatic raw material used in the preparation according to the invention may be any aromatic, i.e. odoriferous, molecule, but is not necessarily an aromatic molecule in the chemical sense of the word. For example, an aromatic raw material may be chosen from:

- aromatic, terpenic and/or sesquiterpenic hydrocarbons, and more particularly essential oils containing these molecules, even more particularly essential oils of citrus (lemon, orange, grapefruit or bergamot) or of nutmeg,
- aromatic alcohols, and more particularly benzyl alcohol, phenylethyl alcohol and phenylpropyl alcohol,
- primary, secondary or tertiary, saturated or unsaturated, cyclic or acyclic nonaromatic alcohols, and more particularly linalol, citronellol, geraniol, nerol, 2,6-dimethyl-7-octen-2-ol, terpineol, and fatty alicyclic alcohols whose chain contains from 4 to 10 carbon atoms,
- aldehydes, and more particularly saturated or unsaturated alicyclic fatty aldehydes whose carbon chain contains from 4 to 12 carbon atoms, aromatic aldehydes such as cinnamaldehyde, (α-amylcinnamaldehyde, α-hexylcinnamaldehyde, butyl-phenylmethylpropional (known under the brand name Lilial), and phenolic aromatic aldehydes such as vanillin and ethylvanillin,
- phenols and more particularly aromatic phenols such as eugenol, isoeugenol and also the methyl ethers thereof,
- carboxylic acids, mainly in their following form:
    - esters, and more particularly acetic esters of benzyl alcohol, of geraniol, of citronellol, of nerol, of terpineol, of borneol or of linalol,
    - esters of aromatic acids such as benzoates and salicylates and also cinnamates esterified with alcohols of the aliphatic series containing a carbon-based chain of 1 to 6 carbon atoms,
    - aromatic phenol-acids, mainly in their lactone/aromatic form, such as coumarin and dihydrocoumarin,
    - carboxylic alcohol acids in their lactone form, and more particularly gamma-octa, gamma-nona, gamma-undeca, gamma-dodeca, delta-deca, delta-undeca and delta-dodeca lactones in their saturated or unsaturated form, and also macrocyclic lactones whose carbon-based chain contains from 12 to 16 carbon atoms,
- aromatic and/or nonaromatic ethers and acetals in their acyclic or cyclic form, and more particularly acetals of aldehydes with a carbon-based chain containing from 4 to 10 carbon atoms and also substituted or unsubstituted furanyl or pyranyl cyclic ethers,
- heterocycles containing a nitrogen atom, and more particularly indole derivatives, and also heterocycles containing two nitrogen atoms, and more particularly derivatives of the pyrazine series,
- ketones, in particular aromatic ketones such as 4-(p-hydroxyphenyl)-2-butanone, and saturated or unsaturated, cyclic or noncyclic nonaromatic ketones,
- aromatic or nonaromatic sulfides, disulfides, and mercaptans.

The preparation according to the invention also comprises one or more meltable excipients of cosmetic grade or suitable for use in household products.

The meltable excipients that may be used are excipients that are suitable for allowing both the protection of the aromatic raw material and the controlled release and shaping in the form of microbeads. They may be chosen from:

- fatty alcohols such as cetyl alcohol, behenyl alcohol, cetostearyl alcohol and stearyl alcohol,
- fatty acids such as stearic acid, myristic acid, behenic acid and palmitic acid,
- glycerol esters such as: glyceryl palmitostearate, glyceryl stearate and glyceryl tribehenate,
- hydrogenated oils such as hydrogenated castor oil, hydrogenated palm oil, hydrogenated corn oil and hydrogenated jojoba oil,
- fatty acid salts such as magnesium stearate, calcium stearate and sodium stearate,
- waxes such as microcrystalline waxes, white wax, carnauba wax and paraffin,
- polyoxyethylene glycols of high molecular weight, sold under the name Carbowax,
- plant fats such as karite butter and monoi oil,
- fatty acid esters such as isopropyl myristate, cetyl palmitate, glyceryl stearate and isopropyl palmitate,
- alkylmethylsiloxanes such as stearyl dimethicone and cetyl dimethicone.

At least 40% by weight, preferably from 60% to 90% and more preferably from 70% to 80% of excipient(s) will preferably be used.

From 0.1% to 60% of aromatic raw material, more preferably from 10% to 40% and even more preferentially from 20% to 30% will be used.

Certain excipients are particularly suitable for obtaining a delayed effect, i.e. a delayed release of the aromatic raw material. Nonlimiting examples that may be mentioned include fatty acids, glycerol esters, hydrogenated oils, waxes, alkylmethyl siloxanes and esterified polyoxyethylene glycols.

Needless to say, a person skilled in the art will select the excipient(s) such that they are inert with respect to the volatile aromatic raw material.

The preparation according to the invention is particularly suitable for highly volatile aromatic raw materials that are particularly fragile and difficult to bind. This is the case especially for 2,6-dimethyl-7-octen-2-ol (known under the brand name Dihydromyrcenol) or methyl dihydrojasmonate (known under the brand name Hedione).

2,6-Dimethyl-7-octen-2-ol or methyl dihydrojasmonate will preferably be used with one or more of the following excipients: fatty acid salts, glycerol esters, hydrogenated oils, alkylmethyl siloxanes, waxes, esterified polyoxyethylenes, plant fats.

In a particularly preferred manner, 2,6-dimethyl-7-octen-2-ol will be used with a mixture of waxes with an alkylmethyl siloxane. A mixture of excipients containing at least 20% of an alkylmethyl siloxane will be more particularly preferred.

The process for manufacturing preparations according to the invention is detailed below. In simplified terms, the aromatic raw material is mixed with one or more meltable excipients in molten form, so as to form a molten mass. Next, the molten mass is forced through a nozzle and the microbeads obtained are cooled. It is essential during the process not to use temperatures that are too high or for too long, otherwise the volatile aromatic raw material will be deteriorated. More specifically, it is known that odoriferous raw materials must not be exposed to excessively high temperatures or to excessively long heating (maximum temperature from 70 to 100° C. depending on the duration of heating, which may be between a few seconds and 4 hours), otherwise they will be impaired and lose their properties and thus their value. Any manufacturing process will thus have to comply with this limitation.

It is occasionally desirable to add other components to the aromatic raw material and to the excipient(s), i.e. to the molten mass.

Thus, one or more polymers that are soluble or dispersible in the molten mass may be added. These polymers will allow a controlled and adjustable dissolution of the microbeads to be promoted during their use in a cosmetic composition. Any suitable polymer may be used, such as:
- cellulose derivatives (hydroxypropylcellulose, hydroxypropylmethylcellulose, hydroxyethylcellulose, ethylcellulose, carboxymethylcellulose),
- acrylic resins,
- polyvinyl acetates,
- allyl methacrylate cross polymers,
- polyalkylene resins (ethylene propylene), polylactic resins, maleic anhydride resins and silicone resins.

One or more mineral additives that allow, with the excipients, the acceleration of the solidification of the microbeads, in particular when the aromatic raw materials show a superheating phenomenon, may also be added to the molten mass. Examples of such additives that may be mentioned include:
- silicas,
- mineral oxides such as titanium oxide or iron oxide,
- phosphates,
- carbonates,
- clays,
- talc.

In order to improve the dispersion or solubility of the aromatic raw material in the excipient(s), it is occasionally useful to add one or more surfactants. By way of example, such surfactants will be chosen from propylene glycol dicaprylate/dicaprate, sorbitan esters, polyethoxylenated alcohols, and glycols such as glycerol or dipropylene glycol.

Moreover, an antioxidant such as vitamin E, and optionally a colorant, may also be added to the preparation.

Thus, the preparation according to the invention comprises:
- a volatile aromatic raw material or a mixture of volatile aromatic raw materials,
- one or more meltable excipients,
- optionally one or more polymers that are dispersible in the molten mass formed by the components of the preparation,
- optionally one or more mineral additives,
- optionally one or more surfactants,
- optionally one or more antioxidants,
- optionally one or more colorants.

As stated above, the process for preparing microbeads consists in preparing a molten mass of the excipient(s) and also of the other optional components, and then in mixing this molten mass with the volatile aromatic raw material. This molten mass may be prepared by separate melting of the various constituents, followed by mixing them with the aromatic raw material, or by melting the mixture of constituents followed by mixing with the aromatic raw material. The optional insoluble components or components that are particularly volatile are added at the end of melting so as to obtain a uniform mass.

The choice of aromatic raw material and of the various components of the molten mass is made by a person skilled in the art on the basis of the compatibility of the constituents, the viscosity of the mixture, the lipophilicity of the aromatic raw material, the particle size of the optional insoluble compounds, the melting point of the aromatic raw material, the size of the desired microbeads, the amount of aromatic raw material to be included therein, the desired release time of the aromatic raw material and the desired melting point of the microbeads.

The microbeads according to the invention may have a melting point between 10° C. and 90° C., preferably between 25° C. and 70° C. and more preferably between 30° C. and 40° C. or 50° C. and 60° C. The conditions for storing the microbeads will depend on their melting point. Microbeads with a high melting point may be stored at higher temperatures than microbeads with a low melting point. By way of example, microbeads with a melting from 25° C. to 30° C. will preferably be stored and handled at a temperature below 10° C. or formulated in a hydrogel.

Preferably, the diameter of the microbeads according to the invention will be between 5 µm and 5 mm, preferably between 10 µm and 4 mm and even more preferably between 10 µm and 1500 µm. In general, the higher the melting point of the microbeads, the smaller the microbeads will preferably be, so as to expose a maximum heat exchange area to the skin, allowing them to melt quickly.

Several known processes may be used to prepare the microbeads according to the invention. For example, the process for manufacturing microbeads described in patent FR 2 657 257 may be used to prepare the microbeads according to the invention with the proviso of the maximum temperature limit and duration that is compatible with the materials used. This process consists in a first step in mixing the active principle (volatile aromatic raw material) with the molten excipient(s) and then in forcing the molten mass through a nozzle which undergoes a vibration, after which the microbeads formed are allowed to fall into a tower countercurrentwise to a gas introduced into the bottom of the tower, and to be removed below the nozzle, the microbeads being formed in the bottom of the tower.

Other processes for manufacturing microbeads may be used, for example the technique of spray cooling, with the same proviso.

The preparation according to the invention may be used in cosmetics, i.e. in a composition for the body, the skin or the hair. They may thus be used in the following cosmetic compositions, which are given as examples:
- fragrancing products, such as solid perfume,
- bodycare and facialcare products, such as milk, cream and hydrogel,
- rinse-out foaming products, such as shampoo and shower gel,
- conditioning products, such as fixing hair gel and conditioner,
- sun creams.

They may also be used to formulate household products such as, for example, detergents, washing powders or washing liquids, and softeners.

Example 1

Highly volatile raw materials which compose the notes cyclamen, lily of the valley, jasmine, gardenia, rose petal and mandarin are protected when they are used in the microbeads according to the invention. They withstand a test of 1 month at 50° C., and the persistence of these very light molecules on the skin or the hair is improved.

Example 2

Microbeads according to the invention are prepared, using the following compounds:
- volatile aromatic raw material or mixture of volatile aromatic raw materials (fragrance): 0.1 to 60% by weight,
- alkylmethyl siloxanes: at least 40% by weight.

These are, for example:
- DC 2503 Cosmetic Wax from Dow Corning, which has a melting point of 32° C., or AMS-C30 Cosmetic Wax from Dow Corning, which has a melting point of 70° C., or a mixture of the two.

other compounds: 0 to 49.8% by weight and preferably 0.1 to 49% by weight, antioxidant, for example BHT or Oxynex 2004:0 to 0.1% by weight and preferably 0.01% to 0.10% by weight, hydrophobic colorants: qs.

Microbeads with melting points ranging between 25 and 70° C., and a diameter of between 50 μm and 2 mm are prepared in the following manner: the meltable materials are heated and the aromatic raw materials are added to obtain a totally liquid mixture. The mixture obtained is poured drop-wise into 96° alcohol denatured with triethyl citrate, and microbeads are obtained.

A nozzle 1 mm in diameter, with or without a vibrator, fed by a temperature-controlled pumping system connected to a temperature-controlled stirring tank to store the mixture of fragrance/alkylmethyl siloxane/other constituents in liquid form, may be used. The mixture falls into the alcohol and sets to form perfectly round microbeads. The dropping medium may be in motion and/or may be temperature-controlled. Microbeads with a diameter of between 500 μm and 4 mm will be obtained depending on the procedure.

Once the microbeads have been formed, the microbeads/alcohol mixture is placed in a refrigerator at 4° C., and the microbeads are then recovered by filtration. To avoid phenomena of sweating and of sticking together of the microbeads, aerosil may be added to the microbeads, and the excess aerosil will be blown off with cold air.

A spray-cooling process may also be used, which will give microbeads of smaller diameter, of the order of 50 μm to 500 μm.

Example 2A

Composition for preparing microbeads according to the invention

| Component | Manufacturer | weight % |
|---|---|---|
| Stearyl dimethicone (DC 2503) | Dow Corning | 74.95 |
| Vitamin E acetate | BASF | 5.00 |
| Fragrance (mixture of aromatic raw materials) | MANE | 20.00 |
| Liposoluble colorant Blue Covapate W 6763 | Wackherr | qs |
| Oxynex antioxidant (BHT, ascorbyl palmitate, citric acid, glyceryl stearate, propylene glycol) | Merck | 0.05 |

The microbeads obtained are formed using a nozzle, have a melting point between 25 and 30° C. and a diameter of between 800 and 1600 μm. They are stored and handled at temperatures below 10° C. or formulated in a hydrogel. The finished product comprising the microbeads, i.e. the body gel, may be packaged in an Airless packaging of the type such as the Magic Dispenser F from the company WIKO.

This solid preparation may be used in a body gel, the composition of which is as follows:

| Component | Manufacturer | weight % |
|---|---|---|
| PHASE A | | |
| Carbomer (Ultrez 10) | Gattefosse | 0.30 |
| Propylene glycol | | 3.50 |
| Demineralized water | | qs 100 |
| PHASE B | | |
| Glycerol | | 5.00 |
| Ethanol (96° alcohol) | | 20.00 |
| Allantoin | Merck | 0.10 |
| Dimethicone copolymer (Abill B 8851 D) | Goldschmidt | 1.00 |
| DMDM hydantoin (glidant) | Lonza | 0.20 |
| PHASE C | | |
| Microbeads according to the above table | Mane | 1.00 |
| PHASE D | | |
| Triethanolamine | | to pH 5.50 |
| Colorant | Wackherr | Qs |
| PPG-7 ceteareth (Eumulgin L) | Henkel | 2.00 |
| Liquid fragrance | Mane | 0.30 |

Example 2B

Composition for preparing microbeads according to the invention:

| Component | Manufacturer | Weight % |
|---|---|---|
| Stearyl dimethicone (DC 2503) | Dow Corning | 51.95 |
| C30-45 alkyl methicone (AMS C-30) | Dow Corning | 25.00 |
| Vitamine E acetate | BASF | 3.00 |
| Fragrance (mixture of aromatic raw materials) | MANE | 20.00 |
| Liposoluble colorant (Brown Covapate W 8760) | Wackherr | Qs |
| Oxynex antioxidant (BHT, ascorbyl palmitate, citric acid, glyceryl stearate, propylene glycol) | Merck | 0.05 |

The microbeads obtained are formed by spray-cooling or prilling, have a melting point of between 50 and 57° C. and a diameter of between 50 and 500 μm. They are stored and handled at temperatures below 30° C. or formulated in a hydrogel.

This solid preparation may be used in a shampoo or shower gel.

The composition of such a shampoo is given below by way of example:

| Component | Manufacturer | weight % |
|---|---|---|
| PHASE A | | |
| Carbomer (Carbopol EDT 2001) | Gattefosse | 1.00 |
| Propylene glycol | | 10.00 |
| Demineralized water | | qs 100 |

-continued

| Component | Manufacturer | weight % |
|---|---|---|
| PHASE B | | |
| TEA-lauryl sulfate (Texapon T42) | Henkel | 15.00 |
| Cocamidopropylbetaine (Tegobetaine HS) | Goldschmidt | 5.00 |
| Ethylene glycol (Emkanol) | | 2.00 |
| DMDM hydantoin (glidant) | Lonza | 0.20 |
| PHASE C | | |
| Microbeads according to the above table | Mane | 1.00 |
| PHASE D | | |
| Triethanolamine | | to pH 5.50 |
| Colorant | Wackherr | qs |
| Liquid fragrance | Mane | 0.30 |

The composition of such a shower gel is given below by way of example:

| Component | Manufacturer | weight % |
|---|---|---|
| PHASE A | | |
| Acrylates/vinyl isodecanote cross polymer (Stabilen 30) | 3V Sigma | 0.50 |
| Propylene glycol | | 2.00 |
| Demineralized water | | qs 100 |
| PHASE B | | |
| Sodium lauryl sulfate (Texapon N40) | Henkel | 20.00 |
| Cocamidopropylbetaine (Tegobetaine HS) | Goldschmidt | 5.00 |
| Ethylene glycol (Emkanol) | | 2.00 |
| DMDM hydantoin (glidant) | Lonza | 0.20 |
| PHASE C | | |
| Microbeads according to the above table | Mane | 1.50 |
| PHASE D | | |
| Sodium hydroxide (aqueous 10% solution) | | to pH 7 |
| Colorant | Wackherr | qs |
| Liquid fragrance | Mane | 0.70 |

Example 3

A test is performed in order to evaluate the persistence of microbeads according to the invention. The test is carried out on an expert panel of 20 individuals, consisting of fragrance manufacturers and evaluators.

The same fragrance is applied to each of the 20 individuals in two different forms: 0.015 g of liquid fragrance on one forearm, and microbeads according to the invention on the other forearm. The evaluation of the decrease in odor (in %) is carried out by each person at different times (in hours) after the application: t=0, 1 h, 2 h and 5 h.

The averages of these estimations are represented on the histogram below, in white for the liquid fragrance and in gray for the microbeads.

Histogram 3:

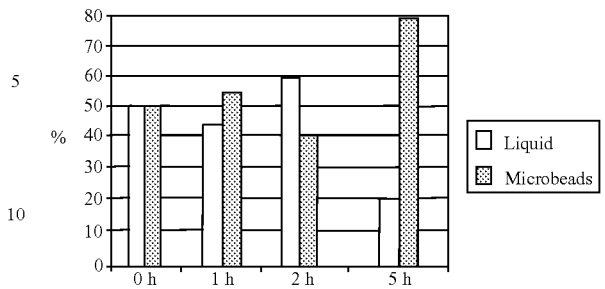

It is clearly observed that the microbead form becomes markedly more effective than the liquid fragrance 5 h after application to the skin, which proves the high persistence of the microbeads.

Example 4

Microbeads according to the invention are prepared using the following compounds:

| Component | Manufacturer | weight % |
|---|---|---|
| Alkylmethyl siloxanes (DC 2503) | Dow Corning | 45.00 |
| Hydrogenated jojoba wax | Jan Dekker | 35.00 |
| Fragrance: Axal fragrance | Mane | 20.00 |

The microbeads, obtained according to the process of the invention, have a melting point of between 50° C. and 65° C. with a diameter of between 5 μm and 40 μm.

These microbeads are formulated in an unconcentrated softening laundry liquid, the composition B of which is given below:

| Component | Manufacturer | weight % |
|---|---|---|
| Dihydrogenated palmoylethyl hydroxyethylmonium methosulfate (Rewoquat WE 28) | Witco | 5.65 |
| Demineralized water | | qs 100 |
| Axal microbeads | Mane | 1.50 |

Another softener is prepared by replacing the microbeads with 0.3% by weight of Axal fragrance in liquid form (composition A).

A fragrance persistence test is performed for the two presentation forms, corresponding to the two softening compositions A and B. The test is carried out on an expert panel of 20 individuals, consisting of fragrance manufacturers and evaluators.

It is carried out with strips of cotton fabric which have undergone a standard washing cycle in a washing machine set at a temperature of 45° C. Each washing machine contains 2 kg of laundry, and the softener load (composition A or B) is 100 g.

After the wash cycle, each panel member designates the strip of fabric that has the strongest fragrance odor. The evaluations are carried out at t=0 (wet laundry) and then at t=24, 48 and 96 hours (dry laundry).

The results are given on the histogram below, in white for the liquid fragrance (composition A) and in gray for the microbeads (composition B):

Histogram 4:

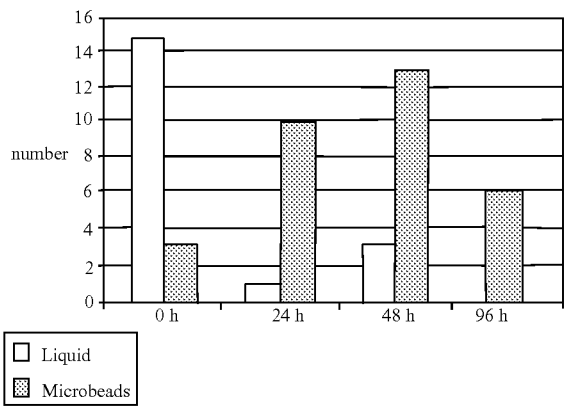

It is clearly observed that the fragrance in the from of microbeads becomes more effective (greater olfactory persistence) than the liquid fragrance at and above a time t=24 h, and this phenomenon continues at t=48 h and t=96 h.

The present invention thus makes it possible to promote the binding of aromatic molecules, in particular of molecules used as a head note in the fragrance industry, and the protection of these molecules used alone or as a mixture in a medium which may be rich in inhibitory active materials, such as hydrogen peroxide and dihydroxyacetone.

The invention claimed is:

1. A solid fragranced preparation with increased persistence in the form of round microbeads obtained from forcing a molten mass through a nozzle, wherein the microbeads consist essentially of:
   10 to 40% by weight of a volatile aromatic raw material or a mixture of volatile aromatic raw materials,
   60 to 90% by weight of meltable excipients comprising one or more meltable alkylmethyl siloxanes and none or at least one meltable excipient selected from the group consisting of fatty alcohols, fatty acids, glycerol esters, hydrogenated oils, fatty acid salts, waxes selected from the group consisting of microcrystalline waxes, white wax, carnauba wax and paraffin, polyethylene glycols of high molecular weight, plant fats, and fatty acid esters, and
   none or at least one member of the group consisting of polymers that are soluble or dispersible in the molten mass, mineral additives, surfactants, antioxidants, colorants, and any combination thereof, wherein polymers soluble or dispersible in the molten mass are selected from the group consisting of cellulose derivatives, acrylic resins, polyvinyl acetates, allyl methacrylate cross polymers, polyalkylene resins, polylactic resins, maleic anhydride resins, silicone resins, and any combination thereof, and
   wherein the microbeads have a melting point between 25° C. and 45° C.

2. The solid fragranced preparation of claim 1, wherein 70% to 80% by weight of meltable excipients are present in the microbeads.

3. The solid fragranced preparation of claim 1, wherein 20% to 30% by weight of volatile aromatic raw material or mixture of volatile aromatic raw materials are present in the microbeads.

4. The solid fragranced preparation of claim 1, wherein the volatile aromatic raw material or mixture of volatile aromatic raw materials is selected from the group consisting of aromatic, terpenic and/or sesquiterpenic hydrocarbons; aromatic alcohols; primary, secondary or tertiary, saturated or unsaturated, cyclic or acyclic nonaromatic alcohols; aldehydes; phenols; carboxylic acids; aromatic and/or nonaromatic ethers and acetals in their acyclic or cyclic form; heterocycles containing a nitrogen atom; ketones; aromatic or nonaromatic sulfides, disulfides and mercaptans, essentials oils, and any combination thereof.

5. The solid fragranced preparation of claim 1, wherein the volatile aromatic raw material or mixture of volatile aromatic raw materials is selected from the group consisting of 2,6-dimethyl-7-octen-2-ol, methyl dihydrojasmonate, and any combination thereof.

6. The solid fragranced preparation of claim 1, wherein the microbeads have a diameter of between 5 µm and 5 mm.

7. The solid fragranced preparation of claim 6, wherein the microbeads have a diameter of between 10 µm and 4 mm.

8. The solid fragranced preparation of claim 7, wherein the microbeads have a diameter of between 10 µm and 1500 µm.

9. A cosmetic composition comprising a solid fragranced preparation of claim 1.

10. The cosmetic composition of claim 9, selected from the group consisting of freelancing products, bodycare and facialcare products, rinse-out foaming products, conditioning products, and sun creams.

11. The cosmetic composition of claim 9, in a form selected from the group consisting of a solid perfume, a milk, a cream, a hydrogel, a shampoo, a shower gel, a fixing hair gel and a conditioner.

12. A household product comprising a solid fragranced preparation of claim 1.

13. The household product of claim 12, selected from the group consisting of detergent products, softening products and textile treatment products.

14. A method for manufacturing a preparation of a solid fragrance with increased persistence in the form of round microbeads, said method consisting essentially of:
   mixing 10% to 40% by weight of a volatile aromatic raw material or a mixture of volatile aromatic raw materials with 60% to 90% by weight of meltable excipients comprising one or more meltable alkylmethyl siloxanes and none or at least one meltable excipient selected from the group consisting of fatty alcohols; fatty acids; glycerol esters; hydrogenated oils; fatty acid salts; waxes selected from the group consisting of microcrystalline waxes, white wax, carnauba wax, and paraffin; polyoxyethylene glycols of high molecular weight; plant fats; and fatty acid esters; to obtain a molten mass;
   adding to the molten mass none or at least one member of the group consisting of polymers that are soluble or dispersible in the molten mass, mineral additives, surfactants, antioxidants, colorants, and any combination thereof wherein polymers soluble or dispersible in the molten mass are selected from the group consisting of cellulose derivatives, acrylic resins, polyvinyl acetates, allyl methacrylates cross polymers, polyalkylene resins, polylactic resins, maleic anhydride resins, silicone resins, and any combination thereof;
   forcing the molten mass through a nozzle to obtain round microbeads; and
   cooling the round microbeads to obtain solidified products, wherein the temperature reached during the method does not exceed 100° C. depending on the duration of heating, which is between a few seconds and 4 hours, and wherein the microbeads obtained have a melting point between 25° C. and 45° C.

15. A solid fragranced preparation with increased persistence in the form of round microbeads prepared by the method of claim 14.

16. The solid fragranced preparation of claim 15 formulated in a hydrogel.

* * * * *